United States Patent [19]

Coker et al.

[11] 4,120,877

[45] Oct. 17, 1978

[54] OXIDATION OF OLEFINS TO OXIRANE COMPOUNDS WITH PERIODATE COMPOUNDS

[75] Inventors: William P. Coker; Robert E. Lane, Jr., both of Lake Jackson, Tex.

[73] Assignee: The Dow Chemical Company, Midland, Mich.

[21] Appl. No.: 834,609

[22] Filed: Sep. 19, 1977

[51] Int. Cl.² ............................................. C07D 301/12
[52] U.S. Cl. ............................ 260/348.23; 260/348.24
[58] Field of Search ....................... 260/348.21, 348.18, 260/348.19, 348.22, 348.23, 348.24

[56] References Cited

U.S. PATENT DOCUMENTS 3,548,012  12/1970  Cornforth ........................ 260/348.21

OTHER PUBLICATIONS

H. Remy, Treatise on Inorganic Chemistry (1956) vol. I, p. 814.
Chatterjee et al., Analytical Chem., vol. 28, No. 5, pp. 878–879 (May, 1956).

Primary Examiner—Norma S. Milestone
Attorney, Agent, or Firm—J. G. Carter

[57] ABSTRACT

Olefins such as propylene are oxidized to the corresponding oxirane with periodate compounds such as potassium periodate at temperatures of 100° C to 400° C.

16 Claims, No Drawings

OXIDATION OF OLEFINS TO OXIRANE COMPOUNDS WITH PERIODATE COMPOUNDS

BACKGROUND OF THE INVENTION

The present invention pertains to a new process for oxidizing olefins.

Olefins have been oxidized to form oxirane compounds by various methods such as by the dehydrochlorination of chlorohydrins, (P. P. McClellan, Ind. Eng. Chem., Vol. 42, 12 (1950), pp. 2402-7) the reaction of hydroperoxides with olefins in the presence of catalysts (U.S. 3,351,635 and R. Landau, et al., Seventh World Petroleum Conference Proceedings, Vol. 5, (1967), pp. 67-72) and uniquely, ethylene can be converted to ethylene oxide by the direct vapor phase oxidation of ethylene with air or oxygen in the presence of a silver catalyst. Olefins have also been oxidized to form oxirane compounds by treatment with organic peracids such as peracetic acid, monoperphthalic acid and perbenzoic acid (U.S. Pat. No. 3,341,556 and Chem. Revs. Vol. 45, (1949) pp. 16-25).

The present invention therefor provides an alternate method for the preparation of oxirane compounds from compounds containing olefinic unsaturation, said method having the following characteristics:
1. A relatively high selectivity to the oxirane product,
2. a minimum of non-useful by-products,
3. no organic co-product,
4. versatility in that various olefins can be epoxidized by the process of the present invention,
5. the process can be conducted where the periodate is in the liquid or solid state,
6. the separation of the oxirane compounds from the periodate is relatively easy, especially when the periodate is a solid.

SUMMARY OF THE INVENTION

The present invention is a process for preparing an oxirane compound by reacting a compound containing olefinic unsaturation or mixture thereof with a periodate compound having the formula (I)—$MIO_4$, (II)—$MH_4IO_6$, or (III)—$M_2H_3IO_6$ wherein M is a monovalent metal or an ammonium radical.

DETAILED DESCRIPTION OF THE PREFERRED EMBODIMENTS

Suitable periodate compounds which can be employed herein as represented by the formulas $MIO_4$ and $MH_4IO_6$ include, for example those compounds wherein M is lithium, sodium, potassium, rubidium, cesium, silver and an ammonium radical represented by the formula $R_4N^+$ wherein each $R_4$ is independently hydrogen or a hydrocarbon group having from 1 to about 8 carbon atoms such as, for example, methyl, ethyl, propyl, butyl, octyl, phenyl, and the like.

Suitable compounds which can be employed herein as represented by the formula $M_2H_3IO_6$ include, for example, those compounds wherein M is lithium, sodium, silver, potassium, rubidium, cesium, and an ammonium radical represented by the formula $R_4N^+$ wherein $R_4$ is defined as above. Mixtures of any of the periodate compounds can also be employed.

Olefinically unsaturated materials which are epoxidized in accordance with the present invention include substituted and unsubstituted aliphatic and alicyclic olefins which may be hydrocarbons, esters, alcohols, ketones, ethers or the like. Preferred compounds are those having from about 2 to 30 carbon atoms, and preferably at least 3 carbon atoms. Illustrative olefins are ethylene, propylene, normal butylene, isobutylene, the pentenes, the methyl pentenes, the normal hexenes, the octenes, the dodecenes, cyclohexenes, methyl cyclohexene, butadiene, styrene, methyl styrene, vinyl toluene, vinylcyclohexene, the phenyl cyclohexenes, and the like. Olefins having halogen, oxygen, sulfur, phosphorus, nitrogen and the like substituents can be used. Such substituted olefins are illustrated by allyl alcohol, methallyl alcohol, cyclohexenol, diallyl ether, methyl methacrylate, methyl oleate, methyl vinyl ketone, allyl chloride, triallyphosphite, triallylphosphate, triallylamine and the like. In general, all olefinic materials epoxidized by methods previously employed can be epoxidized in accordance with this process including olefinically unsaturated polymers having up to about several thousand carbon atoms. Illustrative olefins are linseed oil, olive oil, soybean oil, cottonseed oil, tall oil glycerides, castor oil, corn oil, butyl-polyglycol esters of unsaturated fatty acids, liquid or solid polybutadiene, polyisoprene, unsaturated copolymers of ethylene and propylene including terpolymers thereof with cyclopentadiene and the like.

The ratio of periodate compound to olefin is from about 1:1 to about 1:100, preferably from about 1:5 to about 1:20 moles of periodate:mole of unsaturation.

The temperature employed in the present process can vary from about 100° C. up to about 400° C. The particular temperature which may advantageously be employed depends upon the particular periodate employed. A suitable temperature can be easily determined in the laboratory by gradually raising the temperature of a mixture of the particular periodate and olefin until the corresponding oxirane compound is detected by the appropriate analytical method such as, for example, gas chromatography. In general, increasing the temperature beyond this point will increase the rate of formation of the oxirane compound.

Another method is to heat the particular periodate compound and observe that temperature at which significant quantities of oxygen are released.

Suitable temperatures for some of the periodate compounds employed in oxidizing propylene are as follows:

| Periodate Compound | Temperature ° C |
|---|---|
| $LiIO_4$ | 119-160 |
| $Li_2H_3IO_6$ | 129-135 |
| $NaIO_4$ | 190-350 |
| $NaIO_4$ | (170-240)* |
| $Na_2H_3IO_6$ | 180-214 |
| $KIO_4$ | 260-300 |
| $KIO_4$ | (221-285)* |
| $RbIO_4$ | 271-280 |
| $CsIO_4$ | 158-300 |
| $AgIO_4$ | 165-350 |
| $Ag_2H_3IO_6$ | 109-149 |
| $Bu_4NIO_4$ | 123-140 |

The time of reaction is dependent upon the temperature and residence time of the olefin, but usually is from about 1 second to about 2 hours, but anytime sufficient to provide a suitable conversion at the desired temperature can be employed.

Pressures which can be employed range from subatmospheric pressure to superatmospheric pressure, generally from 1 psia to 200 psig.

The process is easily conducted by contacting the olefin with the periodate compound either in the solid state or in solution. When the periodate compound is in a solution, the olefin can be bubbled through the solution of the periodate compound. When the periodate compound is in the solid state, the olefin can be passed through a bed of the solid material.

The resultant oxidized products can be separated from the periodate compounds by any suitable means such as filtration, distillation or combinations thereof and the like.

The periodates may be employed in their natural form, e.g. crystalline solid or power, may be dissolved in suitable inert solvents or supported on suitable supports.

Suitable solvents are those which are capable of dissolving the periodate complex but which do not react with the periodate at an appreciable rate under the reaction conditions employed. These may include such polar and non-polar solvents as water and aromatic and substituted amide types such as, for example, benzene, biphenyl, dimethylformamide, dimethylacetamide, mixtures thereof and the like.

Suitable supports include inert inorganic solids such as, for example, alumina, silica, silicon carbide, molecular sieves, zirconia, cobalt (II, III) oxide, cerium (IV) oxide, Fuller's earth and the like.

If desired, the olefins may be diluted with an inert material before coming into contact with the periodate. Suitable such inert materials include, for example, the well known inert gases such as nitrogen, helium, argon, and the like.

The periodate compounds if not commercially available can be prepared by the addition of a suitable metal hydroxide to periodic acid ($H_5IO_6$) in mole ratio of acid to hydroxide of from about 1:1 to about 2:1.

The periodate compounds can be prepared by the methods disclosed in "Analytical Applications of Periodic Acid and Iodic Acid and Their Salts" by G. Frederick Smith, 5th Ed. published by The G. Frederick Smith Chemical Co., Columbus Ohio, 1950, Chapter II.

Other ways of preparing the alkali metal periodate include the reaction of the metal iodide or iodate with $Cl_2$ or $Br_2$ in the presence of MOH. The periodate can be prepared by the oxidation of the iodate to a periodate with $K_2S_2O_8$, in the presence of MOH. In preparations where the $M_3H_2IO_6$ (inactive for the epoxidation of an olefin) is the product, it can be converted to the active $MIO_4$ with $HNO_3$.

In the process for making epoxides from olefins and periodates, the periodates are converted to iodates. These iodates can then be converted to periodates by contacting the iodates with oxygen or an oxygen source such as air at temperatures of from about 150° C. to about 400° C. and as high as 800° C. until the desired periodate is formed. Inactive $M_3H_2IO_6$ periodates can be converted to active $M_2H_3IO_6$ periodates by contacting them with weak acids at temperatures of from about 25° C. to about 100° C. until the desired periodate is formed.

The desired oxirane compound can be separated from the other reaction products by any convenient means such as, for example, by distillation, extraction, combinations thereof and the like.

The following examples are illustrative of the present invention but are not to be construed as to limiting the scope thereof in any manner.

EXAMPLE 1

A feed gas containing propylene with or without nitrogen as an inert diluent was passed through a glass tube in which five grams of solid potassium metaperiodate, $KIO_4$, was suspended on glass wool. The tube was heated and the effluent gas stream was analyzed by gas chromatography for the oxidation products. The products of the reaction were later verified by a combination of mass spectroscopy and gas chromatography. Periodic tests were made for carbon dioxide formation by bubbling the effluent through a saturated aqueous solution of calcium oxide. The results are given in the following Table I.

TABLE I

| Run No. | Feed (cc/min.) $C_3H_6$ | $N_2$ | Temp. (° C) | $C_3H_6$ Conv. (%) | Selectivity (%) Acetaldehyde | Propylene Oxide | Propionaldehyde | Acrolein | Acetone |
|---|---|---|---|---|---|---|---|---|---|
| 1 | 95 | — | 275 | — | 19 | 73 | 0.3 | 8 | 0.3 |
| 2 | 95 | — | 280 | — | 16 | 78 | 0.3 | 5 | 1 |
| 3 | 95 | — | 285 | — | 23 | 71 | — | 6 | — |
| 4 | 1 | 4 | 295 | 56 | 16 | 54 | 4 | 19 | 7 |
| 5 | 1 | 4 | 300 | 60 | 14 | 52 | 3 | 16 | 14 |
| 6 | 1 | 4 | 290 | 38 | 19 | 48 | 3 | 21 | 8 |

EXAMPLE 2

A stream of propylene and oxygen was passed over solid $AgIO_4$ and the effluent analyzed by gas chromatography for the formation of oxidation products as the temperature was increased. A 0.3% yield of propylene oxide was observed at 165° C. and was found to have increased to 5% at 350° C.

EXAMPLE 3

Solid $KIO_4$, 3 grams, was finely ground and sprinkled onto a glass wool pad which was then rolled up and placed in a glass reaction tube in a tube furnace. The effluent was connected to a gas chromatograph through a gas sample valve. The reactor was purged with ethylene, the flow rate, 10 cc/min., was established and the temperature slowly raised. Periodic samples of the effluent were taken to identify the oxidation products which were formed. At 280° C., 60% of the oxidation products was found to be ethylene oxide with the remaining 40% being acetaldehyde. A similar experiment in which $NaIO_4$ was used also produced ethylene oxide as the major oxidation product.

EXAMPLE 4

Five grams of finely powdered $NaIO_4$ was placed in the reaction tube described in the previous example. A stream of nitrogen was bubbled through a container of allyl alcohol immediately before the vapors entered the top of the reaction tube. The effluent from the lower end of the reactor was passed through a cold, 0° C., carbon tetrachloride scrubber to remove the oxidation products. The reactor was heated from room temperature to 240° C. Analysis of the trap at this time showed that glycidol had been produced from the reaction of allyl alcohol and sodium metaperiodate.

EXAMPLE 5

The reaction between $NaIO_4$ and propylene under pressure was studied by placing approximately 1 g. of $NaIO_4$ in a 12 × ⅜ inch stainless steel "U" tube. The pressures and flow rates were selected by adjustment of a regulator in the propylene line and a needle valve attached to the outlet of the reactor. The temperature of the reactor was controlled by placing it in a molten nitrate salt bath at 225° C. Analysis of the effluent was made by gas chromatography. Propylene at 15.0 psig and an exit rate of 50 cc/min. gave a selectivity to propylene oxide of greater than 90% based on the organic oxidation products. When the pressure was increased to 29.5 psig and flow rate reduced to 20 cc/min., the selectivity to propylene oxide was found to also be in excess of 90%.

EXAMPLE 6

Two grams of the periodate being evaluated was placed in a glass "U" tube reactor between glass wool plugs. The propylene flow was adjusted to either 15 cc/min. or 5.4 cc/min. The reactor was placed in a molten salt bath at about 200° C. and the temperature slowly increased until gas chromatographic analysis of the effluent showed that oxidation of the propylene was taking place. The results are given in the following Table II.

TABLE II

| Run No. | Periodate | Temp. (° C) | Residence Time (sec.) | $C_3H_6$ Conv.(%) | Selectivity (%) | | | |
|---|---|---|---|---|---|---|---|---|
| | | | | | Acetaldehyde | Propylene Oxide | Propionaldehyde + Acrolein | Acetone |
| 1 | $NaIO_4$ | 238 | 12 | 19 | 2 | 98 | — | — |
| 2 | $NaIO_4$ | 238 | 12 | 11 | 3 | 97 | — | — |
| 3 | $NaIO_4$ | 238 | 12 | 15 | 5 | 95 | — | — |
| 4 | $KIO_4$ | 272 | 14 | 13 | 8 | 92 | — | — |
| 5 | $KIO_4$ | 280 | 14 | 16 | 8 | 92 | 0.5 | — |
| 6 | $KIO_4$ | 284 | 14 | 21 | 8 | 90 | 1 | 2 |
| 7 | $RbIO_4$ | 271 | 18 | 13 | 4 | 96 | — | — |
| 8 | $RbIO_4$ | 272 | 18 | 14 | 4 | 96 | — | 0.2 |
| 9 | $CsIO_4$ | 277 | 22 | 16 | 11 | 89 | 1 | — |
| 10 | $CsIO_4$ | 277 | 22 | 19 | 8 | 91 | 1 | — |
| 11 | $CsIO_4$ | 277 | 22 | 29 | 2 | 96 | 1 | 0.1 |

EXAMPLE 7

A sample of $LiIO_4$, 1 g., was placed in a "U" tube reactor between glass wool plugs. The flow of propylene was adjusted to 50 cc/min. and the reactor immersed in a molten salt bath at 150° C. The temperature was raised to 175° C. at which point gas chromatographic analysis of the effluent showed the organic oxidation products to be 92% propylene oxide and 8% acetone.

EXAMPLE 8

A sample of solid $NaIO_4$ was placed in a reaction tube. A stream of helium was bubbled through cyclohexene and then allowed to pass into the reactor. At about 240° C. gas chromatographic analysis of the effluent showed the formation of cyclohexene epoxide. A corresponding experiment in which $KIO_4$ was used produced cyclohexene epoxide at 265° C.

EXAMPLE 9

As propylene was being passed over a sample of disilver paraperiodate, $Ag_2H_3IO_6$, the temperature of the reactor was gradually increased. Gas chromatographic analysis of the effluent showed that propylene oxide began to be produced at about 110° C. and reached a maximum between about 130° C. and 140° C.

EXAMPLE 10

1-butene was passed over a sample of disodium paraperiodate, $Na_2H_3IO_6$. As the temperature was slowly increased, the effluent stream was analyzed by gas chromatography for the formation of oxidation products. At about 200° C., 6% of the 1-butene was being converted with a selectivity to 1,2-epoxybutane of 79% while the balance went to carbon dioxide.

EXAMPLE 11

Nitrogen was bubbled through cyclohexene and was then allowed to pass into a reactor containing $Na_2H_3IO_6$. As the temperature was increased, the effluent stream was analyzed by gas chromatography for the formation of oxidation products. At around 200° C., 18% of the cyclohexene in the feed gas was found to be converted to cyclohexene oxide.

EXAMPLE 12

An 8 gram sample of $Na_2H_3IO_6$ was placed in a ⅜ × 12 inch tube reactor and held in position by glass wool plugs. After thoroughly purging the reactor with propylene, the temperature was raised from ambient to about 200° C. and held until gas chromatographic analysis of the effluent indicated the conversion of the propylene had dropped below 1%. For this experiment, an average conversion of about 3% of the propylene was obtained with a selectivity of 90% to propylene oxide.

EXAMPLE 13

A 4 gram sample of $Li_2H_3IO_6$ was reacted with propylene at about 130° C. as in the preceding example. A conversion of 3% was obtained with a selectivity of 37% to propylene oxide.

EXAMPLE 14

A 1:1 mixture of propylene and nitrogen was passed over a silicon carbide support to which 5% $NaIO_4$ had been added. At a reaction temperature of 238° C. gas chromatographic analysis of the effluent indicated a 7% conversion of the propylene with an 82% selectivity to propylene oxide.

EXAMPLE 15

An experiment similar to Example 14 using an 8% add-on of $CsIO_4$ resulted in a maximum selectivity of 56% to propylene oxide. In a further experiment 1% add-on of $Na_2CO_3$ was made after the 8% $CsIO_4$; the resulting selectivity to propylene oxide was found to have increased to 70%.

EXAMPLE 16

A 1:1 mixture of ethylene and nitrogen was passed over a silicon carbide support to which 10% $NaIO_4$ had been added. Ethylene oxide was identified in the effluent by gas chromatography at a reaction temperature of 245° C.

EXAMPLE 17

Quantities of 5%, 15%, 50%, 85% and 95% $NaIO_4$ were added onto a $Co_3O_4$ support from water solution of the $NaIO_4$. The quantities were % by weight of the $Co_3O_4$ support. Samples of these supported periodates were placed in a glass reactor and immersed in a constant temperature bath. Propylene and oxygen were passed over the samples and the temperature was raised in 10° C. increments. At each temperature, the effluent was analyzed by gas chromatography. For these mixtures a threshold temperature for propylene oxide formation of 170°-180° C. was found, where the normal threshold temperature for sodium metaperiodate is 210°-220° C.

EXAMPLE 18

A similar series of experiments using $KIO_4$ showed a similar reduction in the threshold temperature for the formation of propylene oxide from the normal 270°-280° C. to 220°-230° C.

EXAMPLE 19

A sample of tetrabutylammonium periodate, $Bu_4NIO_4$, and benzene was placed in an autoclave which was sealed, pressurized with propylene and heated to about 130° C. for 1½ hours. Gas chromatographic analysis of the benzene solution showed the formation of propylene oxide.

EXAMPLE 20

When propylene was bubbled through a solution of tetrabutylammonium periodate in biphenyl at atmospheric pressure, gas chromatographic analysis of the effluent showed the oxidation of propylene to propylene oxide would proceed with better than 95% selectivity at a reaction temperature between about 120° C. and 140° C.

EXAMPLE 21

When $LiIO_4.2.6H_2O$ (or $LiH_4IO_6.0.6H_2O$) was dissolved in either dimethylformamide or dimethylacetamide and propylene bubbled through the solutions, propylene oxide was found to be formed at reaction temperatures between about 125° C. and 140° C.

EXAMPLE 22

Water and $LiIO_4.2.6H_2O$ was placed in an autoclave which was sealed, pressurized with propylene and heated to 160° C. Gas chromatographic analysis of the water showed the formation of 1% propylene oxide.

EXAMPLE 23

A ten gram sample of $NaIO_4$ was placed in a glass "U" tube reactor. The nitrogen feed to the reactor was bubbled through a second "U" tube, filled with styrene at about 73° C., immediately before it entered the reactor. As the reactor was heated from about 200° C. to 240° C., the effluent was scrubbed through a toluene filled trap at about 0° C. Analysis of this trap at the conclusion of the reaction showed styrene oxide to be the major reaction product.

EXAMPLE 24

Trans-2-butene was passed through a glass "U" tube containing 3.0 gram of $NaIO_4$ at a rate of approximately 15 cc/min. The effluent was scrubbed through a water filled trap which was cooled in an ice bath. Trans-2,3-epoxybutane was the major product observed in the water trap as the reactor was heated from about 210° C. to 245° C. In a similar experiment using cis-2-butene was the olefin, cis-2,3-epoxybutane was the major product observed in the water trap at a reaction temperature of about 220° C.

EXAMPLE 25

A 1 × 24 inch glass tube reactor was charged with 200 grams of $Na_2H_3IO_6$ and heated to 215° C. under a propylene flow of 500 cc/min. The effluent stream was scrubbed by passing it through four consecutive gas wash bottles containing water at 0° C. Gas chromatographic analysis of the reactor effluent indicated a peak propylene conversion of 6% after 1 hour with a 93% selectivity to propylene oxide. The periodate activity essentially ceased (less than 1% propylene conversion) after 2 hours at temperature and the residue was cooled and analyzed for iodate and periodate. The average propylene conversion and selectivities based on the vapor phase analysis along with the periodate oxygen selectivities for the run were:

| | Conv. | Carbon Dioxide | Selectivities | | |
| --- | --- | --- | --- | --- | --- |
| | | | Propylene Oxide | Water | Oxygen |
| Propylene | 3 | 6 | 94 | — | — |
| Periodate-Oxygen | 26 | 18 | 50 | 9 | 24 |

Analysis of each of the scrub solutions indicated a total of 4.5 grams of propylene oxide had been collected which on a molar basis corresponds to 3% of the propylene passed.

The first of the scrub solutions, consisting of 200 cc of 1.5% propylene oxide in water and containing 2/3 of the propylene oxide produced, was distilled on a ½ inch × 1 foot helices packed column. The initial reflux temperature was 34° C. and 2.2 gram of distillate was collected at this temperature and up to 50° C. A second fraction of 2.3 g was collected between 50° and 100° C. Chromatographic analysis indicated the first fraction had the following composition:

94% propylene oxide, 1% acetaldehyde, 1% Acrolein and 4% water.

This composition was confirmed by infrared and mass spectrometric analysis. The second fraction analyzed 6% propylene oxide, 94% water. The balance of the propylene oxide (0.7 gram) not recovered in the first or second fraction was accounted for in the bottoms as propylene glycol.

What is claimed is:

1. A process for forming an oxirane compound from a compound containing olefinic unsaturation which comprises contacting said compound containing olefinic unsaturation or a mixture thereof with a periodate represented by the formulas $MIO_4$, $MH_4IO_6$ and $M_2H_3IO_6$ or their hydrates, wherein M is a monovalent metal selected from lithium, sodium, potassium, rubidium, cesium, and silver or an ammonium group represented by the formula $R_4N^+$ wherein each R is independently a hydrocarbon group having from about 1 to about 8 carbon atoms, at a temperature, pressure and time sufficient to form said oxirane compound and thereafter recovering said oxirane compound.

2. The process of claim 1 wherein the periodate is represented by the formula $MIO_4$ wherein M is K, Li, Na, Rb, Cs, Ag or $Bu_4N^+$.

3. The process of claim 1 wherein the periodate is represented by the formula $MH_4IO_6$ wherein M is Li.

4. The process of claim 1 wherein the periodate is represented by the formula $M_2H_3IO_6$ wherein M is Li, Na or Ag.

5. The process of claim 2 wherein the compound containing olefinic unsaturation is propylene, ethylene, ethyl alcohol, cyclohexene, styrene, cis-2-butene or trans-2-butene.

6. The process of claim 3 wherein the compound containing olefinic unsaturation is propylene, 1-butene or cyclohexene.

7. The process of claim 4 wherein M is K and the temperature is from about 260° C. to about 300° C.

8. The process of claim 4 wherein M is Na and the temperature is from about 190° C. to about 350° C.

9. The process of claim 4 wherein M is Li and the temperature is from about 119° C. to about 350° C.

10. The process of claim 4 wherein M is Rb and the temperature is from about 271° to about 280° C.

11. The process of claim 4 wherein M is Cs and the temperature is from about 158° C. to about 300° C.

12. The process of claim 4 wherein M is Ag and the temperature is from about 165° C. to about 350° C.

13. The process of claim 4 wherein M is $Bu_4N^+$ and the temperature is from about 123° C. to about 140° C.

14. The process of claim 5 wherein M is Li and the temperature is from about 129° C. to about 135° C.

15. The process of claim 5 wherein M is Na and the temperature is from about 180° C. to about 214° C.

16. The process of claim 5 wherein M is Ag and the temperature is from about 109° C. to about 149° C.

* * * * *

UNITED STATES PATENT AND TRADEMARK OFFICE
CERTIFICATE OF CORRECTION

PATENT NO. : 4,120,877
DATED : October 17, 1978
INVENTOR(S) : William P. Coker and Robert E. Lane It is certified that error appears in the above-identified patent and that said Letters Patent are hereby corrected as shown below:

In the second line of the abstract, change "periodiate" to -- periodate --.

In Col. 2, line 16, change "triallyphosphite" to --triallylphosphite--.

In Col. 2, line 62, after the table insert -- *The periodate was supported on $Co_3O_4$. --.

In Col. 3, line 16, change "power" to -- powder --.

In Col. 5, line 20, after "and" insert -- the --.

In Col. 8, line 20, change "was" to -- as --.

In Col. 10, line 1, change "ethyl" to -- allyl --.

In Col. 10, l. 6,8,10,12,14,16 and 18, change "4" to -- 5 --.

In Col. 10, line 20, change "5" to -- 6 --.

Signed and Sealed this

Sixth Day of November 1979

[SEAL]

Attest:

RUTH C. MASON
Attesting Officer

LUTRELLE F. PARKER
Acting Commissioner of Patents and Trademarks